United States Patent [19]

Hadtke

[11] Patent Number: 4,585,445
[45] Date of Patent: Apr. 29, 1986

[54] HYPODERMIC SYRINGE HOLDER FOR USE WITH DISPOSAL AMPOULES

[75] Inventor: Frederick B. Hadtke, New Providence, N.J.

[73] Assignee: Sterling Drug Inc., New York, N.Y.

[21] Appl. No.: 766,630

[22] Filed: Aug. 19, 1985

[51] Int. Cl.[4] ............................................ A61M 5/245
[52] U.S. Cl. .................................................. 604/234
[58] Field of Search ............... 604/234, 232, 187, 218

[56] References Cited

U.S. PATENT DOCUMENTS 1,546,491  7/1925  Kasmaukas .
1,839,695  1/1932  Nevin .
1,843,554  2/1932  Goldberg .
3,092,108  6/1963  Friedman ........................... 604/232
3,115,135  12/1963  Sarnoff ............................. 604/232 X
3,811,441  5/1974  Sarnoff .
4,333,457  6/1982  Margulies ....................... 604/232 X Primary Examiner—John D. Yasko
Attorney, Agent, or Firm—William G. Webb; B. Woodrow Wyatt; Paul E. Dupont

[57] ABSTRACT

Hypodermic syringe holders for use in combination with disposable medicament-containing ampoules are adapted to immobilize the ampoules within the syringe holder so as to provide manual aspirating capability.

10 Claims, 20 Drawing Figures

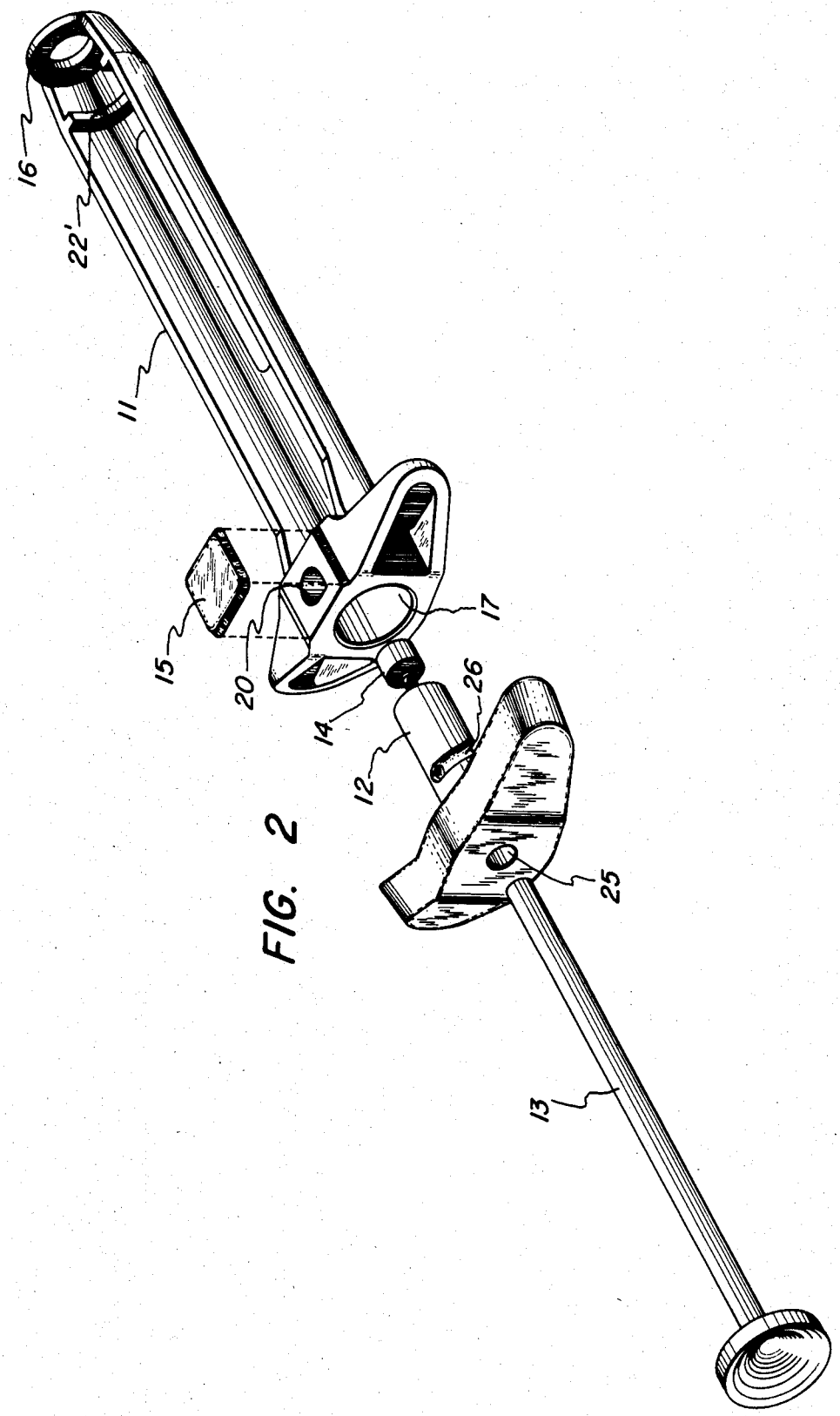

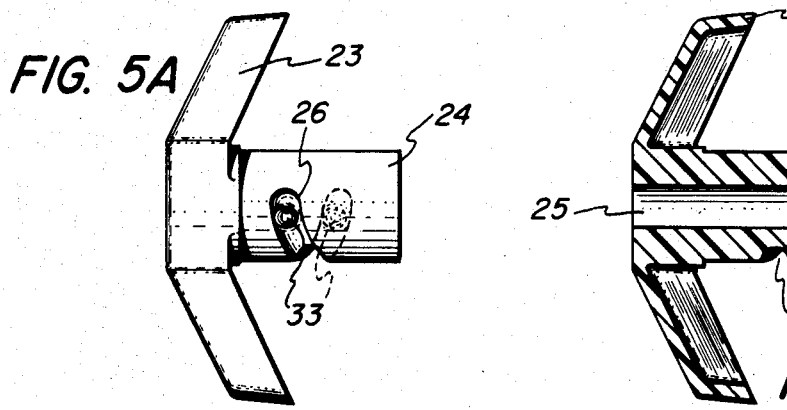
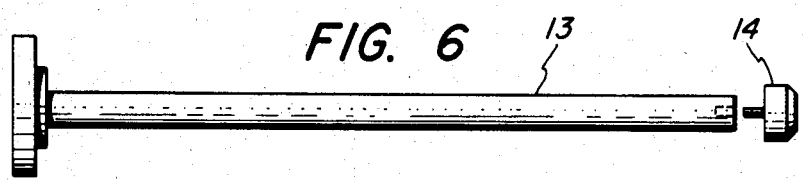
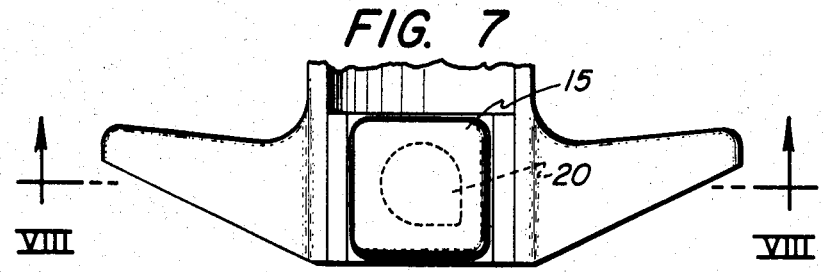
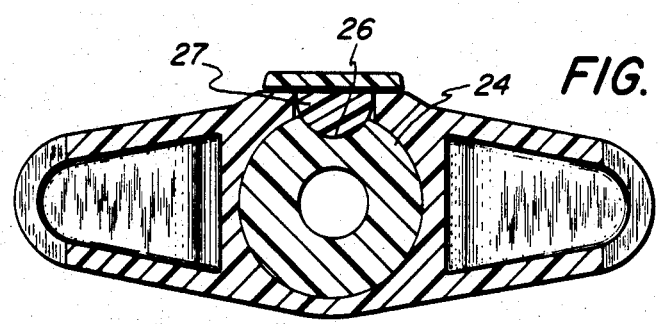

HYPODERMIC SYRINGE HOLDER FOR USE WITH DISPOSAL AMPOULES

BACKGROUND OF THE INVENTION

This invention relates to the field of hypodermic syringe holders for use in combination with disposable medicament-containing ampoules. More specifically, it relates to syringe holders of simple construction which are adapted to easily, and effectively, immobilize a cartridge ampoule within the holder during use. The holders are thus particularly effective for manual aspirating use.

INFORMATION DISCLOSURE STATEMENT

It is desirable, in medical practice, to provide hypodermic syringes with an aspirating capability so as to enable the medical practitioner, after insertion of the hypodermic needle into the injection site, to determine whether the needle has entered a major blood vessel and, depending upon whether blood is drawn back into the syringe during aspiration, and depending also upon the desired route of administration, to either proceed with the injection or to withdraw the needle and relocate it before injection as appropriate to the circumstances.

In general, aspiration in hypodermic syringes can be achieved by adapting the syringe holder for either manual or self-aspiration, depending upon whether aspiration is achieved by generation of a slight negative pressure in the syringe holder by the slight manual withdrawal of the ampoule piston or whether the slight negative pressure is generated by some mechanical action effected by the particular syringe design.

Self-aspirating syringes are often complex in structure and are therefore usually expensive to manufacture. Manually operable aspirating syringes have the potential at least for relative simplicity of construction, because those used with disposable medicament-containing ampoules require only a means to securely hold the ampoule in the syringe holder barrel to prevent axial displacement thereof in the holder and a means to affix the end of the plunger rod of the holder to a slidable piston closing the inner end of the ampoule. With such positive engagement between the plunger and the piston, slight withdrawal of the interconnected plunger/piston generates the essential negative pressure in the ampoule.

The means of achieving the first objective, securing the ampoule against axial displacement in the holder, has conventionally been approached in a variety of ways in the prior art. For example Kasmaukas U.S. Pat. No. 1,546,491 discloses a hypodermic syringe holder comprising two coaxially arranged semi-cylindrical shells which are rotatably and axially movable one within the other. The outer shell has a slot 18 at its upper end which cooperates with a pin 17 set in the wall of the upper end of the inner shell, and the slot is so shaped that by turning the outer shell a half turn in one direction, it will slide rearwardly along the inner shell to form a cylinder for enclosing a medicament capsule, leaving two narrow slots on either side of the cylinder for viewing the capsule within the cylinder. The cylinder thus serves to hold the medicament capsule, and when the outer shell moves rearwardly relative to the inner shell, the capsule stopper 30 is pierced by the inner end of a double-ended needle 28. When the outer shell is rotated in the opposite direction, it moves forward relative to the inner shell, opening up the cylinder for removal of the capsule from the syringe.

Nevin U.S. Pat. No. 1,839,695 discloses a hypodermic syringe holder which is adapted for firmly locking an ampoule, closed at one end with a rubber plug, within the syringe holder prior to use of the same. In one embodiment shown in FIG. 2, the upper end of the syringe holder barrel is closed by a cap 11 having a bore in the end wall to receive a plunger rod which is fitted at its lower end with a head 35 adapted to bear against the ampoule plug. The head of the syringe holder has a sleeve/clamping means 29 within cap 11, and the head can be moved axially backwards and forwards within the bore of the holder by means of a pin handle 41 fitted to the sleeve which extends through an inclined or spiral slot 42 in the wall of the barrel. Thus when the pin is moved to the lower end of the slot, it causes the sleeve or the clamping means 29 to bear against the rim of the ampoule and thus to hold it firmly in position within the barrel. Conversely when the pin is moved to the upper end of the slot, pressure against the ampoule is relieved, and the ampoule can be removed from the holder.

Goldberg U.S. Pat. No. 1,843,554 discloses a syringe holder for use with medicament-containing cartridges. The cartridges are held in place within the barrel of the syringe holder by engagement of its upper end by a rotatable plug 4 having screw threads 5 which coact with interior screw threads 6 in the upper part of the holder.

Sarnoff U.S. Pat. No. 3,811,441 discloses a hypodermic syringe for use in combination with an ampoule assembly. The ampoule is immobilized within the barrel of the syringe holder by a latch cap 38 having a pair of notched latches 40 which interlock with a locking flange 18 at the rim of the syringe holder.

The syringe holders provided by the present invention are of simple construction, accomplish the above-stated objectives in manually aspirating type syringe holders with a minimum number of working parts and are thus inexpensive to manufacture.

BRIEF DESCRIPTION OF THE INVENTION

The present invention comprises an improvement in hypodermic syringe holders of the type wherein an axially movable ampoule clamping element is engaged with the rim of an associated ampoule to securely immobilize the ampoule within the barrel of the syringe holder by rotating the clamping element about its longitudinal axis within the head portion of the holder, the improvement which comprises in combination: a semicylindrical body portion having a generally cylindrical head portion (adapted for side loading through the open side thereof of a medicament-containing ampoule); an axially mounted clamping element rotatable within the head of the body portion and having a helical groove in the side wall thereof; a plunger element having affixed to its lower end a piston engaging means, said plunger element and piston engaging means being axially secured within the bore of the clamping element and axially slidable therein; and a boss element having on its underside a hemispherical portion engageable with the helical groove in the side wall of the clamping element and permanently affixed to the head portion of the syringe holder to thereby secure all elements of the syringe holder together in cooperative engagement with one another.

BRIEF DESCRIPTION OF THE DRAWINGS

FIG. 2 is an exploded perspective view of a syringe holder of the invention showing all the various elements of the holder and their method of assembly.

FIG. 5A is a top view of the clamping element of a syringe holder of the invention.

FIG. 5B is a cross-sectional view of the clamping element of a syringe holder of the invention in the plane of FIG. 5A.

FIG. 6 is a plan view of the plunger element with associated engaging means of a syringe holder of the invention.

FIG. 7 is an enlarged top view of the head of the body portion of a syringe holder of the invention.

FIG. 8 is a cross-sectional view on line VIII—VIII of FIG. 7.

FIGS. 2A, 12B and 12C are end, side and bottom views, respectively, of the alternative boss element and construction depicted in FIGS. 10 and 11.

DETAILED DESCRIPTION OF THE INVENTION

The invention will now be described in detail with reference to the foregoing figures where like numerals are used to identify like parts.

In the foregoing discussion, and elsewhere in the specification and appended claims, the terms "lower" and "downward" are intended to make reference to the needle end of the syringe holder and associated parts, and conversely the terms "upper" and "upward" are intended to make reference to the head end thereof.

Figure 1:
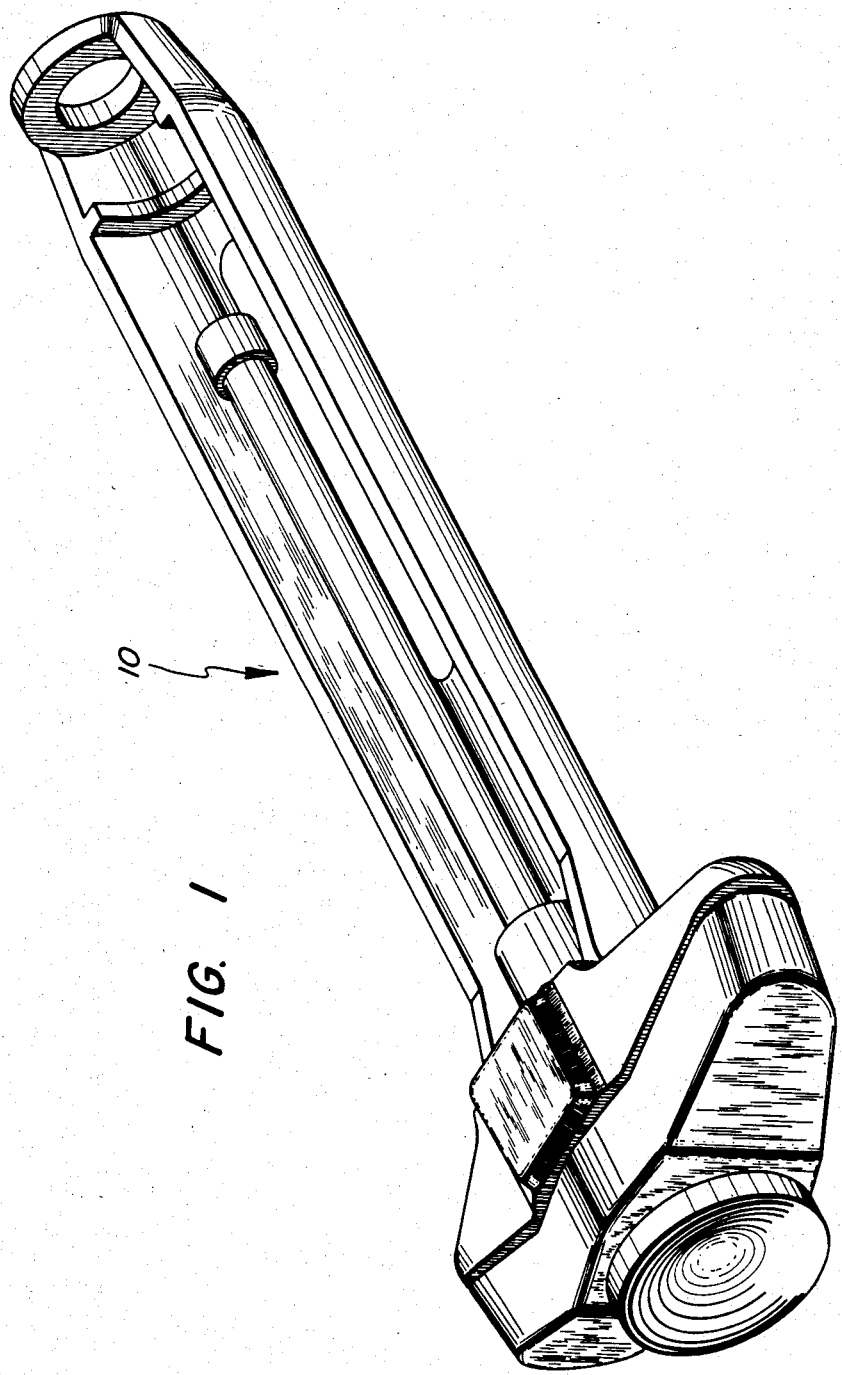
FIG. 1 is a perspective view of a fully assembled syringe holder of the invention.

Referring to FIGS. 1 and 2, the syringe holders of the invention, represented by general reference numeral 10, are intended for use in combination with conventional medicament-containing ampoules which are closed at the upper end with a flexible piston slidable within the bore of the ampoule and closed at the lower necked-down end by a rubber diaphragm secured to the ampoule by a crimped-on metal collar. The necked-down end is conventionally fitted with a needle/needle hub unit and a needle sheath. A typical such ampoule/needle assembly is sold commercially as CARPUJECT ®.

The syringe holder comprises a total of five elements, which are best seen with reference to FIG. 2, namely a generally semi-cylindrical body portion 11; a clamping element 12; a plunger element 13; associated piston engaging means 14; and boss 15.

Figure 3A:
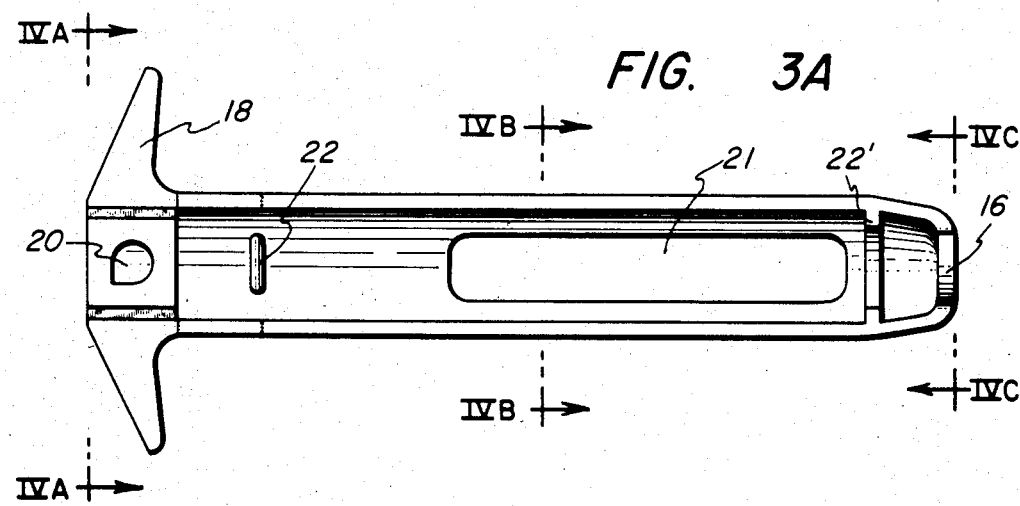
FIG. 3A is a top view of the body portion of a syringe holder of the invention.
Figure 3B:
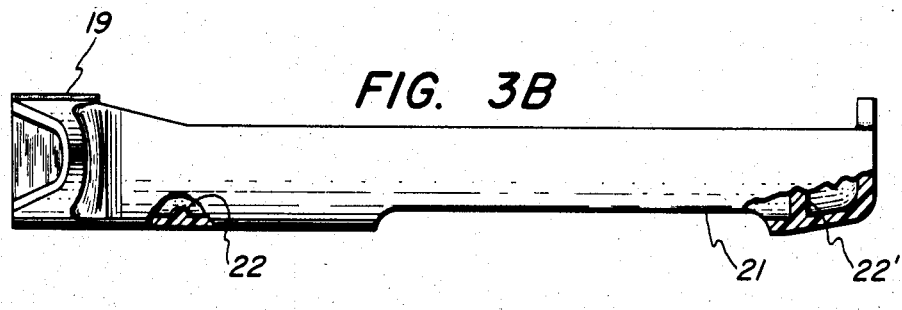
FIG. 3B is a side view of the body portion of a syringe holder of the invention.
Figure 4A:
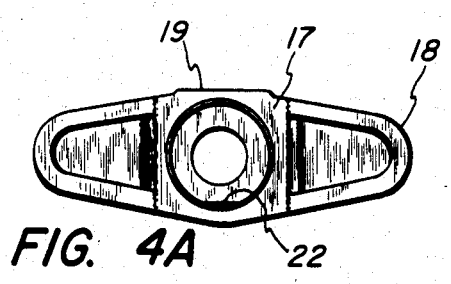
FIG. 4A is a cross-sectional view on line IVa—IVa of FIG. 3A.
Figure 4C:
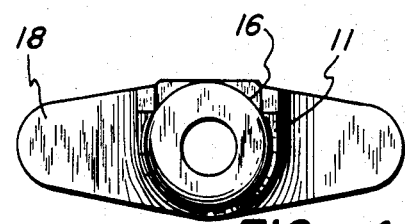
FIG. 4C is a cross-sectional view on line IVc—IVc of FIG. 3A.
Figure 4B:
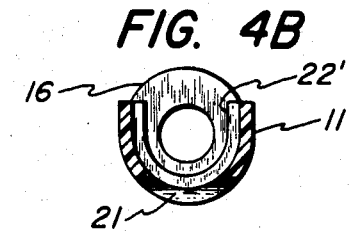
FIG. 4B is a cross-sectional view on line IVb—IVb of FIG. 3A.
Figure 9A:
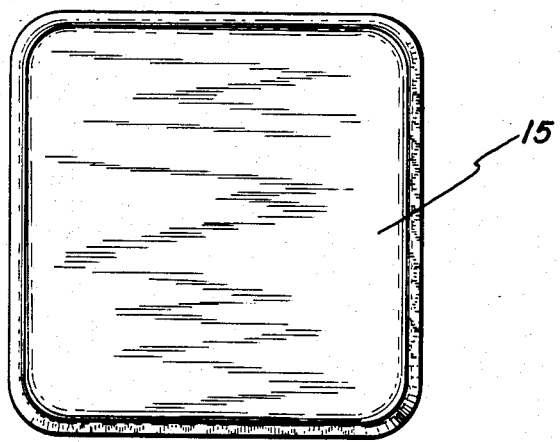
FIGS. 9A, 9B and 9C are top, side and bottom views, respectively, of the boss element depicted in FIGS. 7 and 8.
Figure 9B:
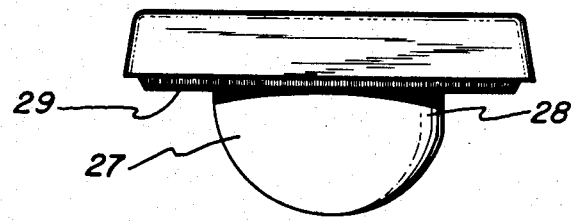
Figure 9C:
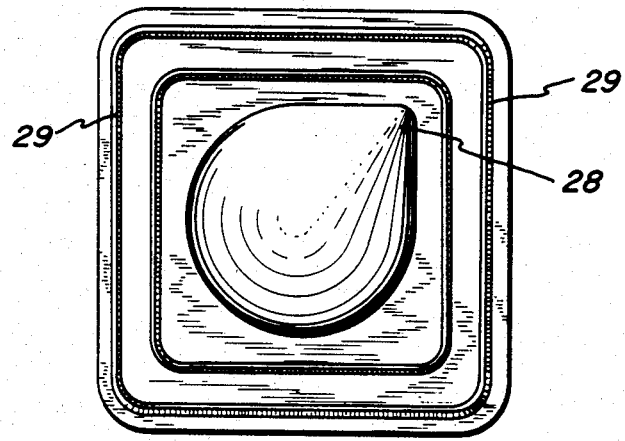
Figure 10:
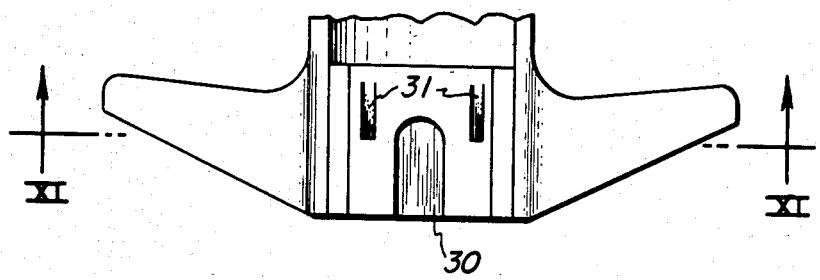
FIG. 10 is an enlarged top view of the head of the body portion showing an alternative construction thereof.
Figure 11:
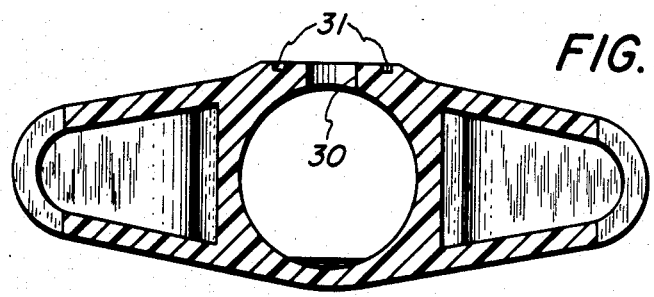
FIG. 11 is a cross-sectional view on line XI—XI of FIG. 10.
Figure 12A:
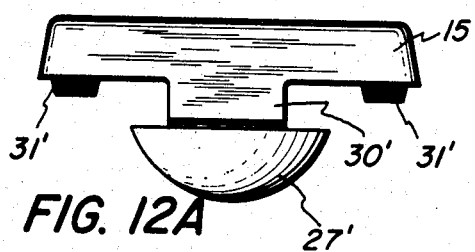
Figure 12B:
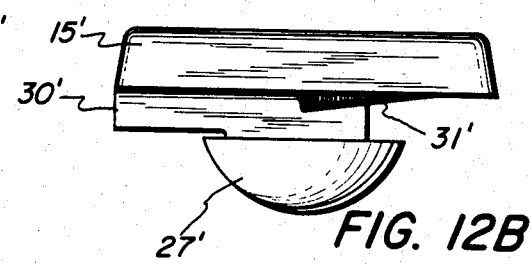
Figure 12C:
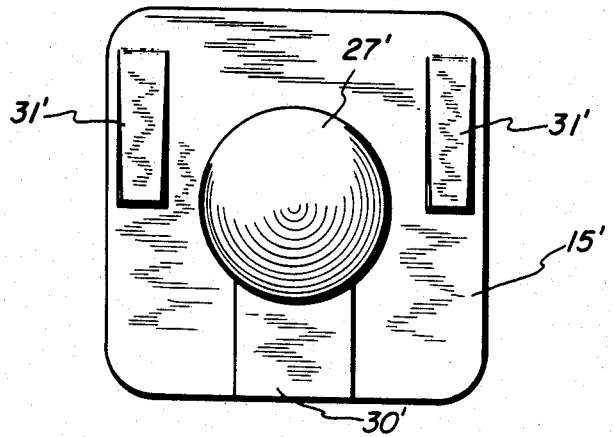

With reference to FIGS. 2, 3A, 3B, 4A, 4B and 4C, the body portion comprises a generally semi-cylindrical unit which is adapted for side-loading of an ampoule through the open side wall. For this purpose the lower end has a circular hole 16 sized to fit around the needle hub of an ampoule/needle/needle hub/needle sheath unit used in combination with the holder. The upper end of the body portion has a short cylindrical section having a bore 17 therethrough for receiving the clamping element 12 which will be described shortly. Finger gripping means 18 are provided for ease of manipulation of the syringe holder in use. The body portion also has a flattened area 19 having a keyhole opening 20 therethrough, the purpose of which will also be described shortly. The holder may also optionally have a viewing window 21, which is desirable when the syringe holder is used as an aspirating syringe. The body portion may also be optionally equipped with raised ribs 22 or 22', located near the upper or lower end, respectively, of the body portion as shown in FIGS. 2, 3A and 3B, which serve to align an ampoule within the body of the syringe holder with the tip of the piston engagement means 14.

The ampoule clamping element 12, shown in FIGS. 5A and 5B, consists of a pair of handles 23 and a barrel 24 having a relatively small diameter bore 25 sized to slidably receive the shaft of plunger rod 13 shown in FIG. 6. The barrel of clamping element 12 has a slightly expanded bore section 25' which is sized to accept the piston engaging means 14, also shown in FIG. 6, and which has a slightly larger diameter than the shaft portion of the plunger. Extending partially around the outer surface of the barrel of clamping element 12 is a helical groove 26.

The helical groove is semi-circular in cross section and is of such width and depth that it will slidably receive a hemispherical lug 27 on the bottom surface of boss 5. The construction of boss 15 and its relationship to clamping element 12 are best seen with reference to FIGS. 7, 8, 9A, 9B and 9C from which it will be seen that boss 15 is generally square in top view and is sized to occupy the generally flattened area 19 located on the cylindrical portion of body portion 11. The hemispherical lug on the bottom of the boss has a tear drop shaped section 28 extending laterally from the hemispherical lug and oriented generally towards a corner of the boss. The hemi-spherical lug 27 and unitary tear drop shaped section are of such shape and size that they fit within the keyhole 20 located on the flattened area 19 of the body portion, and, as seen in FIG. 8, the hemi-spherical lug fits within the helical groove 26 on the barrel of clamping element 12.

With reference to FIG. 2, to assemble the various parts of the syringe holder as described above, the plunger rod 13 is first inserted through the bore 25 of clamping element 12, and the piston engaging means 14 is affixed to the tip of the plunger rod by press fit of a knurled post on the piston engaging means with a mating hole in the tip of the plunger. The resulting clamping means/plunger/piston engaging means sub-assembly is then inserted through the bore 17 of body portion 11, and the clamping element is rotated within the bore so as to expose the helical groove 26 to view through keyhole 20. The hemispherical/tear drop lug section of boss 15 is then aligned with keyhole 20, the hemispherical section is engaged with the helical groove 26, and the boss is affixed in place on the syringe holder by any appropriate means. One means of affixing the boss to the holder when the parts are made of plastic is to provide a pair of beads 29, shown in FIG. 9C, which serve as a means of sonic welding the boss to the syringe holder. All the elements of the syringe holder are thereby joined together in cooperative relationship with one another.

An alternative means of affixing the boss to the holder is shown in FIGS. 10, 11, 12A, 12B and 12C. In that alternative embodiment, the flattened area 19 on the head of the body portion is provided with a slot 30 and a pair of ramped cavities 31 arranged on either side thereof. The boss 15' is molded with hemispherical lug 27' which is located atop and on the inner end of an integral base portion 30' which extends to one edge of the boss and which is sized to fit within slot 30. A pair of ramps 31' is sized and located on the boss to fit within the ramp cavities 31. Thus to assemble the syringe holder in the configuration just described, the plunger rod/piston engaging means/clamping means/body portion sub-assembly discussed peviously is first made. After alignment of the helical groove 26 with slot 30, the end of base portion 30' on the bottom of the boss is aligned with the open end of slot 30, and the boss is forced inward until the hemispherical lug engages helical groove 26, and ramps 31' engage ramp cavities 31. This alternative embodiment is also particularly adaptable to assembly using plastic molded parts.

It will be seen from the above description that, by rotating the clamping means approximately one half revolution in one direction or the other, the clamping means will move either forward to a fully engaged position or backward to a fully retracted position. Thus in use the clamping means is first fully retracted by one half turn in one direction, counterclockwise as illustrated in the drawings, an ampoule/needle/needle hub/needle sheath unit is inserted through the side opening of the syringe holder, and the clamping means is given one half turn in the opposite direction to cause the shoulder 32 of clamping element 12, shown in FIG. 5B, to bear against the rim of the ampoule thus securing it firmly in place within the holder. The plunger is then engaged with the piston of the ampoule, one means of achieving such engagement illustrated here being to turn the plunger rod so as to engage a screw-threaded hole in the end of the piston engaging means 14 with a screw-threaded post on the piston. The clamping element may optionally be equipped with a pair of raised ribs 33, shown in FIG. 5A, located near both ends of helical groove 26 which serve to lock the clamping means either in the fully engaged or the fully retracted positions.

It will be appreciated that minor modifications in the various elements of the invention may be made without departing from the spirit of the invention. For example, the means for accommodating the hub of the ampoule/needle/needle hub/needle sheath unit to the syringe holder has been described herein as a circular hole 16. However, a side opening slot would obviously serve the same purpose, and such means is considered to be within the ambit of the inventive concept here described.

Moreover, the piston engaging means is described herein as being a screw-threaded element which mates with a screw-threaded post on the ampoule piston. Such means of engaging the plunger with the piston, however, is only a preferred means, and other piston engaging means well known in the art will serve the purpose as well. Such other engaging means include, for example, multiple retractable claws or hooks, such as shown in U.S. Pat. No. 2,693,804; a screw-threaded engagement into threads molded into the plunger, such as disclosed in U.S. Pat. No. 2,706,984; fixed claws such as described in U.S. Pat. No. 2,789,559; an expandable chuck, such as disclosed in U.S. Pat. No. 2,869,542; resilient gripping fingers, such as disclosed in U.S. Pat. No. 2,895,473; a barbed point or "harpoon", such as disclosed in U.S. Pat. No. 2,904,044; or a bayonet connection, such as disclosed in U.S. Pat. No. 2,986,141.

Although the various elements of the syringe holders described herein may be made of any suitable material, including metals or plastics, they are well adapted to fabrication of plastic, particularly body portion 11, clamping element 12, plunger element 13 and boss 15, and such method of fabrication of those parts is particularly preferred. Although the piston engaging means 14 can also be made of plastic, it is preferably made of metal, for example brass.

When the various elements are constructed of plastic, suitable plastics are high density polypropylene, polystyrene, ABS (clear or opaque), nylon, DELRIN ® or polyethylene. A particularly preferred plastic is high density polypropylene.

The boss 15, which serves to hold all the elements of the syringe holders together, may in addition to the means specifically illustrated herein, be affixed to the body portion by any other suitable means appropriate to the materials used to construct the holders. When they are constructed of certain plastics, the boss may be affixed to the body portion by, for example, thermal, sonic or solvent welding, gluing and the like. Other plastic materials, not adaptable to joining by such means, may require use of the ramp and ramp cavities method described above. When constructed of metal, they may be affixed by screws through the boss into the head portion, by welding, brazing, gluing or the like.

Having thus described the invention and the advantages thereof, it is considered that the invention is to be broadly construed and limited only by the character of the following claims.

I claim:

1. In a hypodermic syringe holder of the type where an axially movable ampoule clamping element is engaged with the rim of an associated ampoule to securely immobilize the ampoule within the barrel of the syringe holder by rotating the clamping element about its longitudinal axis within the head portion of the holder, the improvement which comprises in combination: a semi-cylindrical body portion having a generally cylindrical head portion; an axially mounted clamping element rotatable about its longitudinal axis within the cylindrical head of said body portion and having a barrel portion, a handle portion and a helical groove on the outer surface of the barrel portion thereof, said clamping element having a bore therethrough with diminished and enlarged portions thereof; a plunger element having affixed to its lower end a piston engaging means, said plunger rod and piston engaging means being axially and slidably receivable within said bore of said clamping element; and a boss element having on its underside a hemispherical portion engageable with said helical groove of said clamping element, said boss being permanently affixed to the head portion of said syringe holder to thereby secure all elements thereof together in cooperative engagement with one another.

2. A syringe holder according to claim 1 having a viewing window in the side of said semi-cylindrical body portion.

3. A syringe holder according to claim 1 having raised ribs near both ends of said helical groove for locking said clamping element in either a fully engaged or fully retracted position.

4. A syringe holder according to claim 1 wherein said piston engaging means comprises a screw-threaded hole in the end thereof for screw-threaded engagement with a screw-threaded post on the piston of said ampoule.

5. A syringe holder according to claim 2 wherein said semi-cylindrical body portion said clamping element, said piston rod and said boss are fabricated of plastic and said boss is secured to the head portion of said semi-cylindrical body portion by sonic welding thereto.

6. A syringe holder according to claim 2 wherein said semi-cylindrical body portion, said clamping element, said piston rod and said boss are fabricated of plastic and said boss is secured to the head portion of said semi-cylindrical body portion by interengagement of ramps on the underside of said boss and ramp cavities on said head portion.

7. A syringe holder according to clam 3 wherein said semi-cylindrical body portion, said clamping element, said piston rod and said boss are fabricated of plastic and said boss is secured to the head portion of said semi-cylindrical body portion by sonic welding thereto.

8. A syringe holder according to claim 3 wherein said semi-cylindrical body portion, said clamping element, said piston rod and said boss are fabricated of plastic and said boss is secured to the head portion of said semi-cylindrical body portion of said semi-cylindrical body portion by interengagement of ramps on the underside of said boss and ramp cavities on said head portion.

9. A syringe holder according to claim 4 wherein said semi-cylindrical body portion, said clamping element, said piston rod and said boss are fabricated of plastic and said boss is secured to the head portion of said semi-cylindrical body portion by sonic welding thereto.

10. A syringe holder according to claim 4 wherein said semi-cylindrical body portion, said clamping element, said piston rod and said boss are fabricated of plastic and said boss is secured to the head portion of said semi-cylindrical body portion by interengagement of ramps on the underside of said boss and ramp cavities on said head portion.

* * * * *

UNITED STATES PATENT AND TRADEMARK OFFICE
CERTIFICATE OF CORRECTION

PATENT NO. : 4,585,445
DATED : April 29, 1986
INVENTOR(S) : Frederick B. Hadtke

It is certified that error appears in the above-identified patent and that said Letters Patent is hereby corrected as shown below:

Column 4, line 37, "boss 5" should read --boss 15--.

Column 5, line 19, "peviously" should read --previously--.

Column 6, line 51, "rotatableabout" should read --rotatable about--.

Signed and Sealed this

Sixteenth Day of October, 1990

Attest:

HARRY F. MANBECK, JR.

*Attesting Officer*   *Commissioner of Patents and Trademarks*